United States Patent
Romo et al.

(10) Patent No.: US 12,419,770 B2
(45) Date of Patent: Sep. 23, 2025

(54) ADJUSTABLE MULTI-BAND SPINE BRACE SYSTEM

(71) Applicant: Aspen Medical Products, LLC, Irvine, CA (US)

(72) Inventors: Albert V. Romo, Lakewood, CA (US); Jane Price, Anaheim, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 109 days.

(21) Appl. No.: 17/687,567

(22) Filed: Mar. 4, 2022

(65) Prior Publication Data

US 2022/0280325 A1 Sep. 8, 2022

Related U.S. Application Data (60) Provisional application No. 63/157,424, filed on Mar. 5, 2021.

(51) Int. Cl.
  *A61F 5/02* (2006.01)
(52) U.S. Cl.
  CPC .................... *A61F 5/028* (2013.01)
(58) Field of Classification Search
  CPC .... A61F 5/028; A61F 5/00; A61F 5/01; A61F 5/02–03; A61F 5/24–37; A41C 1/02; A41C 1/08; A61H 2201/1623; A61H 2205/081
  USPC .................................................. 602/19; 2/44
  See application file for complete search history.

(56) References Cited

U.S. PATENT DOCUMENTS

| | | | |
|---|---|---|---|
| 4,022,197 A | 5/1977 | Castiglia | |
| 4,459,979 A * | 7/1984 | Lewis, Jr. | ............... A61F 5/028 602/19 |
| 4,838,043 A | 6/1989 | Jencks | |
| 5,318,505 A | 6/1994 | Sou | |
| 5,599,287 A * | 2/1997 | Beczak, Sr. | ............. A61F 5/026 128/95.1 |

(Continued)

FOREIGN PATENT DOCUMENTS

| | | |
|---|---|---|
| GB | 2525004 A | 10/2015 |
| WO | 03/088877 A1 | 10/2003 |
| WO | 2005/117769 A1 | 12/2005 |

OTHER PUBLICATIONS

PCT/US2022/019049 filed Mar. 5, 2022 International Search Report and Written Opinion dated Jul. 5, 2022.

(Continued)

*Primary Examiner* — Rachael E Bredefeld
*Assistant Examiner* — Seth R. Brown
(74) *Attorney, Agent, or Firm* — Rutan & Tucker, LLP (57) ABSTRACT

A spine brace features a first and a second arm covering a first and a second side of the patient, respectively. Each arm features a middle band disposed between an upper band and a lower band, and an adjustment mechanism that allows for independent adjustment of each band. Each arm may feature a cord coupled to the pulley base to tighten the brace. The adjustment mechanism may include slots for each of the bands, and the upper and lower slots are angled with respect to the middle slot. The first and second arms are removably coupled together using a hook and loop coupling. The brace further features a T-shaped opening that narrows in a center of the adjustment mechanism.

22 Claims, 5 Drawing Sheets

(56) References Cited

U.S. PATENT DOCUMENTS

| | | | |
|---|---|---|---|
| 5,634,891 A * | 6/1997 | Beczak, Sr. ............ | A61F 5/028 450/119 |
| 5,690,609 A | 11/1997 | Heinze, III | |
| 5,830,168 A | 11/1998 | Finnell et al. | |
| 5,853,378 A * | 12/1998 | Modglin ................. | A61F 5/028 128/100.1 |
| 6,336,908 B1 | 1/2002 | Slautterback | |
| 6,419,652 B1 | 7/2002 | Slautterback | |
| 6,500,137 B1 | 12/2002 | Molino et al. | |
| 7,473,235 B2 | 1/2009 | Schwenn et al. | |
| 12,036,142 B1 | 7/2024 | Fried et al. | |
| 2002/0032397 A1 | 3/2002 | Coligado | |
| 2010/0152636 A1 | 6/2010 | Parks et al. | |
| 2010/0168630 A1 | 7/2010 | Cropper et al. | |
| 2010/0205708 A1 | 8/2010 | Storms, Jr. et al. | |
| 2011/0105971 A1 | 5/2011 | Ingimundarson et al. | |
| 2011/0295169 A1 * | 12/2011 | Hendricks ............... | A61F 5/028 602/19 |
| 2013/0006158 A1 | 1/2013 | Ingimundarson et al. | |
| 2013/0237891 A1 | 9/2013 | Fryman et al. | |
| 2014/0058306 A1 | 2/2014 | Bannister | |
| 2014/0058307 A1 * | 2/2014 | Marshall ................... | A61F 5/02 602/19 |
| 2014/0135672 A1 | 5/2014 | Joseph et al. | |
| 2014/0228727 A1 * | 8/2014 | Burke ..................... | A61F 5/028 602/19 |
| 2017/0325988 A1 | 11/2017 | Nadeau | |
| 2018/0353315 A1 * | 12/2018 | Grim ....................... | A61F 5/028 |
| 2019/0343673 A1 | 11/2019 | Wolanske et al. | |
| 2020/0060860 A1 | 2/2020 | Kramer et al. | |
| 2021/0196029 A1 | 7/2021 | Dabrowka | |
| 2022/0226139 A1 | 7/2022 | Poker et al. | |
| 2022/0280326 A1 | 9/2022 | Romo et al. | |
| 2023/0181346 A1 | 6/2023 | Romo | |

OTHER PUBLICATIONS

U.S. Appl. No. 17/687,592, filed Mar. 4, 2022, Non-Final Office Action dated Mar. 20, 2024.

U.S. Appl. No. 17/687,592, filed Mar. 4, 2022, Final Office Action dated Sep. 23, 2024.

EP22764207.1 filed Oct. 5, 2023, Partial European Search Report dated Dec. 12, 2024.

U.S. Appl. No. 17/687,592, filed Mar. 4, 2022, Notice of Allowance dated Dec. 16, 2024.

U.S. Appl. No. 18/083,358, filed Dec. 16, 2022 Non-Final Office Action dated Jan. 29, 2025.

EP22764207.1 filed Oct. 5, 2023, Extended European Search Report dated Mar. 28, 2025.

U.S. Appl. No. 17/687,567, filed Mar. 4, 2022, Notice of Allowance dated May 14, 2025.

* cited by examiner

ADJUSTABLE MULTI-BAND SPINE BRACE SYSTEM

CROSS-REFERENCE TO RELATED APPLICATIONS

This application claims the benefit of priority on U.S. Provisional Patent Application No. 63/157,424 filed Mar. 5, 2021, the entire contents of which are incorporated by reference herein.

FIELD

Embodiments of the disclosure relate to the field of medical devices. More specifically, one embodiment of the disclosure relates to an adjustable spine brace and components thereof.

GENERAL BACKGROUND

The following description includes information that may be useful in understanding the described invention. It is not an admission that any of the information provided herein is prior art or relevant to the presently claimed invention, or that any publication specifically or implicitly referenced is prior art.

Orthopedic braces (orthoses) usually need to be adjusted or customized in some manner to conform to the body part(s) being braced, and then properly positioned. A typical orthosis commonly has at least two portions, a rigid portion supporting a body part, and a flexible or semi-flexible portion securing the orthosis to the body. Various types of spine braces, such as a thoracic-lumbar-sacral orthosis (TLSO) for example, are used to provide support and stabilization of the spine normally after a back injury and/or surgery, and in some cases, may be utilized to address spinal pathologies. A TLSO is a brace that limits movement in a wearer's spine from the thoracic area (mid-back area) to the wearer's sacrum (lower-back area).

Conventional adjustable braces typically have a narrow anterior region, i.e., the front, and the area where the adjustment is done is typically on the side. A loop-and-hook mechanism is usually used to shorten/adjusting the length of the brace. The adjustment process is vital, as a proper fit of the brace provides the wearer with improved pain reduction and promotes healing. However, one common problem with the adjustment process is that the brace needs to apply the proper compression and stabilization to achieve pain reduction and promoted healing. If the circumference is inadequate or the contours of the belt cannot accommodate the user, the fit (e.g., proper compression and stabilization) will be inadequate. Therefore, there is a need for a spine brace that is easily adjustable to provide proper fit to the wearer.

BRIEF DESCRIPTION OF THE DRAWINGS

Embodiments of the invention are illustrated by way of example and not by way of limitation in the figures of the accompanying drawings, in which like references indicate similar elements and in which.

DETAILED DESCRIPTION

As noted above, conventional adjustable spine braces are adjusted on the side via a loop-and-hook mechanism. Herein, the circumference and contour of the brace can be adjusted to proper relevant circumferential lengths.

Disclosed herein is a spine brace featuring a first arm covering a first side of a patient wearing the spine brace and a second arm covering a second side of the patient, respectively. Each arm features a middle band disposed between an upper band and a lower band, and an adjustment mechanism that allows for independent adjustment of each band. Each arm may feature a cord coupled to the middle band to tighten the spine brace. The adjustment mechanism may include slots for each of the bands, where an upper slot for the upper band and a lower slot for the lower band are angled with respect to a middle slot that is shaped with a narrowing toward a center region of the middle slot. The first and second arms are removably coupled together using a hook and loop coupling or any other suitable coupling mechanism.

As described herein, the adjustment mechanism may be deployed as one or more components of a tightening mechanism such as components of a pulley base forming a part of a pulley system. According to one embodiment of the disclosure, the adjustment mechanism features upper, middle and lower slots formed into a body of the pulley base. The upper and lower slots may be angled with respect to the middle slot to receive the upper band and lower band so that the spine brace may be tapered from a first side closer to the posterior portion of the spine brace to a second side closed to the anterior portion of the spine brace. As described herein, the "spine brace" may constitute any type of lumbar sacral orthosis (LSO), including a standard LSO (lower back brace belt) or other orthoses configured to provide greater patient immobilization, such as a LSO, TLSO or CTLSO as described below.

When deployed as a LSO, TLSO or CTLSO, the brace may be further configured in accordance with the tightening mechanism that includes slots for each of the upper, middle and lower bands.

Each of the components described herein may be formed, at least in part, with a rigid material, such as hardened plastic for example, to provide greater stiffness for immobilization of the wearer, e.g., the patient. In various embodiments, each band is made of different materials. For example, the upper and lower bands are made of a material which may be softer (e.g., provide smoother or cushiony texture based on greater flexibility, looser knit or knit pattern, different chemical composition, different material structure, or the like) than the material from which the middle band is made. Alternatively, at least two of the bands are made of the same type of material. Herein, the posterior portion of the spine brace is shaped and sized to accommodate the mid-to-lower portions of the back to partially immobilize the patient's spine. When worn, the posterior portion is oriented to reside or is substantially in parallel with a frontal plane located at the posterior surface of the patient. It provides support along the thoracic, lumbar and sacral regions of the patient's spine. A lateral portion of each belt arm of the spine brace may cover one side of the patient. Additionally, the anterior portion resides or substantially is parallel with a frontal plane on the anterior surface of the patient, and is in contact with the abdominal region and anterior rib cage of the patient.

The anterior portion of each of the first and second arms may include a coupling section to removably attach to the other anterior portion, e.g., via hook fasteners such as VELCRO® strips. Alternatively, the anterior portion of each of the first and second arms may be removably coupled together by using a hook and loop coupling. The spine brace may be slightly tapered laterally from one side to the other side, in that, while the middle band's width is substantially constant, the upper/lower bands are extended slightly downward/upward to couple the middle band. In some embodiments, this tapered configuration improves the contour of the spine brace and enhances the comfort of the patient.

The tightening mechanism may include a plurality of slots for the bands. The upper and lower slots may be angled with respect to the middle slot to allow the upper band and lower band to extend slightly towards each other to couple with the middle band and forming a slightly tapered spine brace.

In some embodiments, a separate tightening mechanism can be used for each of the first and second arms of the spine brace. Each tightening mechanism may be designated to allow independent tightening of the top or bottom of the corresponding arm.

To facilitate convergence of the upper and lower bands and forming a slightly tapered spine brace, a lower part of the upper slot slightly overlaps with an upper part of the middle slot, and an upper part of the lower slot slightly overlaps with a lower part of the middle slot. The middle slot features an opening with a selected shape, generally referred to as a "T-shaped" opening merely for clarity, which narrows slightly in the center of the tightening mechanism which can further guide the middle cord.

According to some embodiments, the spine brace system may feature one or more pulley bases of a pulley system, each operating as the tightening mechanism. The pulley system featuring a cord and a pair of pulley bases, where each pulley base includes a plurality of pulleys. By tightening the cord that passes through each of the pulleys, the patient can tighten a corresponding upper or lower circumference of the spine brace system.

I. Terminology

In the following description, certain terminology is used to describe aspects of the invention. For example, the term "member" may be construed as a structural component of an orthopedic brace. In certain situations, a member may include a component covered by soft goods such as one or more textiles, one or more fabrics (woven fabrics and/or non-woven fabrics), leathers, and/or another covering material. These soft goods may feature "loop" type fasteners or other variants to which a "hook" type fastener may be attached or may feature a hook-type fastener for attachment to a loop-type fastener. In other situations, the member may be soft goods attached to another structural component of the orthopedic brace such as a textile or fabric sewn to form together such as a knit textile with pockets in which the structural component(s) can be positioned within the pocket(s).

The term "attach" and other tenses of the term (attached, attaching, etc.) may be construed as a physical connection activity, such as physically connecting a first member to a second member. A "fastener" may be construed as any physical component that is used to attach different members together. An illustrative example of different types of fasteners and fastening techniques may include, but are not limited or restricted to snaps, buttons, clasps, buckles, adhesives, sewing, heat sealing (or melting), gluing, knitting, or other physical coupling techniques such as a hook and loop connection.

The terms "rigid" or "rigidity" with respect to a member or portion of a member may be construed as the member being configured to at least partially resist bending or deformation. According to this definition, different lengths of a given structure and composition can be rigid at a shorter length, and flexible at a longer length. As used herein, the term "rigid" with respect to a member or portion of a member may be construed as the member will be permanently deformed or broken if bent or twisted by at least 90°.

The term "softer" may pertain to a characteristic of a first material when compared to a second material, where the level of softness may be a result of differences in the first material from the second material to provide the first material with a smoother or cushiony nature, achievable by the first material having greater flexibility caused by a looser knit, a higher thread count, a different chemical composition, and/or a different structural composition.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. General Architecture

Figure 1A:
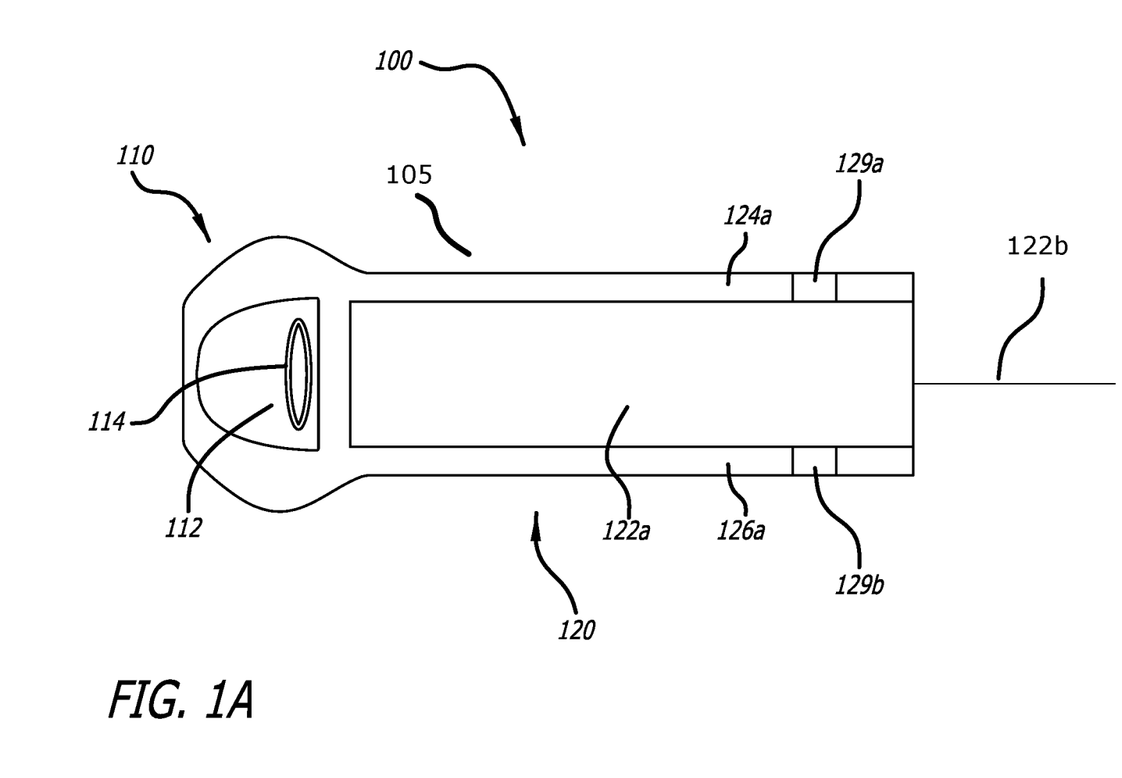
FIG. 1A is a perspective outside view of an exemplary embodiment of an adjustable multi-band spine brace system.

Referring to FIG. 1A, a perspective outside view of an exemplary embodiment of an adjustable multi-band spine brace system 100 is shown. For sake of simplicity, a first arm 105 of the spine brace system 100 is shown. Each arm of the spine brace system 100, such as the first arm 105 of FIG. 1A and a second arm 106 of FIG. 1B, includes an anterior portion 110 (i.e., a front portion), a lateral portion 120, and a posterior portion (i.e., a back portion, not shown). The posterior portion is oriented, when worn, to generally reside or is substantially in parallel with a back plane of the patient. The posterior portion may provide support along a thoracic and lumbar regions of the patient's spine. The lateral portion 120 may cover the sides of the patient. Similarly, the anterior portion 110 is oriented, when worn, to generally reside or is substantially in parallel with a frontal plane of the patient.

The anterior portion 110 may be in contact with the abdominal region and rib cage of the patient's spine.

Figure 1B:
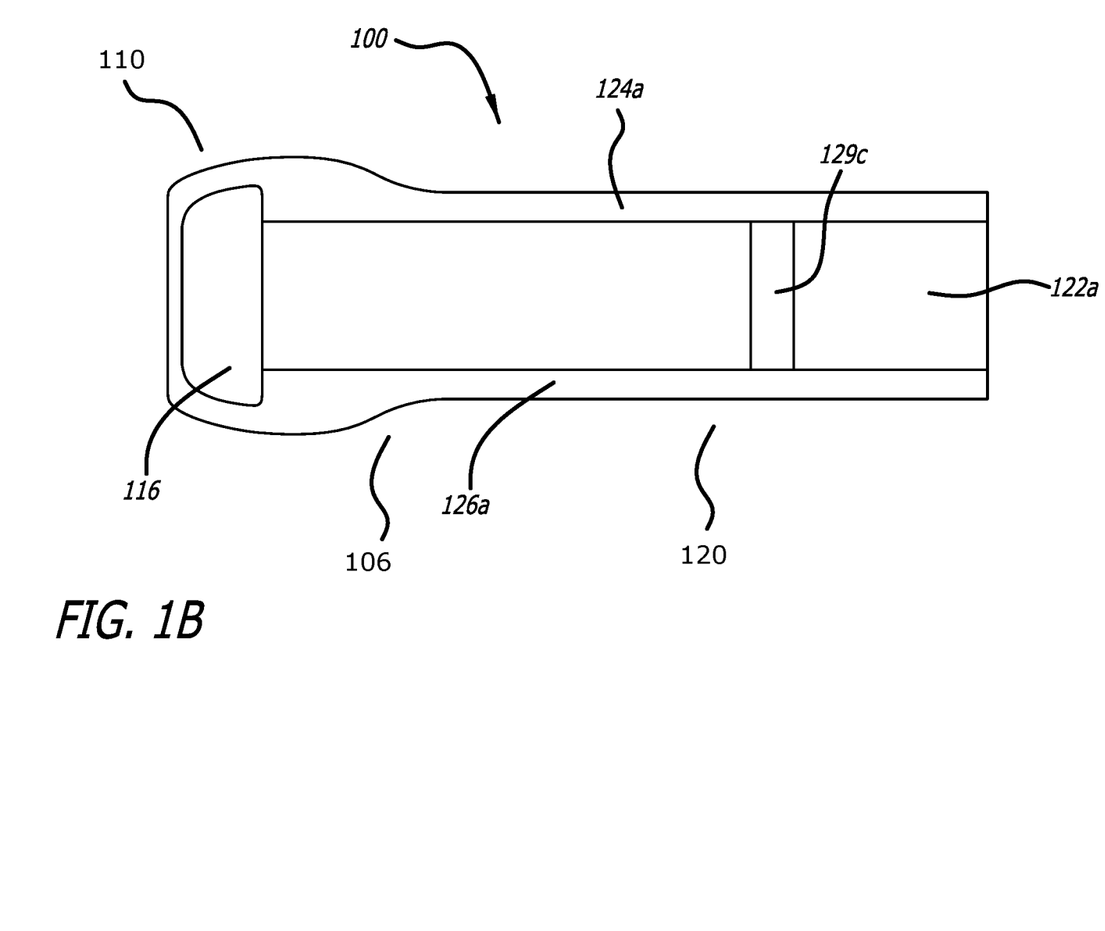
FIG. 1B is a perspective inside view of an exemplary embodiment of an adjustable multi-band spine brace system of FIG. 1A.

Each arm may include a coupling section, such as a coupling 112 for the first arm 105 shown in FIG. 1A, and a coupling 116 for the second arm 106 shown in FIG. 1B, respectively. Each of the coupling sections 112 and 116 is configured to removably attach/couple to the other coupling section. Regardless of the size and shape, the coupling sections 112/116 of the arms 105/106 are so formed that match each other and, when attached/coupled together, form a uniformly closed brace which circumferentially surrounds the body of the patient. Therefore, in some embodiments, the anterior portions 110 of the two arms 105 and 106 of the spine brace system 100 are removably coupled together by using a hook and loop coupling. As a non-limiting example, the coupling section 112 may include a VELCRO® strip or another type of hook fastener while the coupling section 116 may include a loop fastener. In some embodiments, the anterior section 110 may further include a slot 114. This creates a pocket to facilitate better purchase of the fingers during donning.

As shown, the spine brace system 100 further features a middle band 122a disposed between an upper band 124a and a lower band 126a. According to one embodiment of the disclosure, the middle band 122a, the upper band 124a and the lower band 126a are attached/coupled only in one end (e.g., at the posterior portion). That is, the middle band 122a, the upper band 124a and the lower band 126a can operate independent of each other. Each of the upper band 124a, the lower band 126a and the middle band 122a are made of flexible materials that can flex and/or bend around the circumference body of the patient.

In various embodiments, each band 122a, 124a and 126a may be made of different materials. For example, the upper and lower bands 124a and 126a may be made of a same material which may be substantially softer than the material from which the middle band 122a is made. Alternatively, at least two of the bands 122a/124a, 122a/126a, 124a/126a, 122a/124a/126a are made of the same material type. In some embodiments, each band 122a, 124a and 126a is made of a different material. In some embodiments, when worn, the entire upper band 124a, the middle band 122a and the lower band 126a are substantially in contact with each other and form a continuous layer around the body of the patient. By substituting a single-piece band, with three bands, the patient can adjust each portion of the spine brace system 100, e.g., lower, upper, or middle, independently, which results in a better fit and higher stability of the spine brace system 100 to accommodate the contours and circumference of the patient. Further, the three-band configuration described herein enables the patient to tighten each portion (band) of the spine brace system 100 separately, without exerting excessive compressive force on other portions of the body of the patient covered by the spine brace system 100. Additionally, or in the alternative, in some embodiments, portions of the upper band 124a and the lower band 126a may overlap the middle band 122a. Similarly, in some embodiments, portions of the middle band 122a may overlap the upper band 124a and the lower band 126a.

As shown, the middle band 122a, may include an upper fastening mechanism 129a and a lower fastening mechanism 129b. The upper and lower fastening mechanisms 129a and 129b may be used to fasten the corresponding band. As a non-limiting example, the fastening mechanisms 129a, 129b may constitute complementary unbroken loop (UBL) and hook fastener pairs.

Referring to FIG. 1B, a perspective inside view of an exemplary embodiment of a spine brace system 100 of FIG. 1A is shown. As shown, the middle band 122a may include a middle fastening mechanism 129c. Each fastening mechanism may be used to fasten the corresponding band. As a non-limiting example, the fastening mechanism 129c is a hook and loop fastener such as VELCRO®. Since each band 122a, 124a and 126a can operate independently, e.g., the length of each band 122a, 124a and 126a is independent of the other bands, the patient can adjust each of the bands 122a, 124a and 126a separately. This can improve the comfort of the patient since they can adjust the length of each section, i.e., band, based on the needs. For example, the patient may need to increase the length of the upper band 124a after a meal, which can be done by only changing a length of the upper band 124a while the lengths of the other two bands 122a and 126a remain unchanged. While FIG. 1A and FIG. 1B illustrate that the lower and upper fastening mechanisms 129a and 129b are disposed on an opposite side of the middle fastening mechanism 129c, the upper, lower and middle fastening mechanisms 129a, 129b and 129c can be disposed on a same side.

In some embodiments, each band 122a, 124a and 126a folds back on itself by passing through a slot. The details of the slots will be described below. Generally, the patient can pull a portion of a band 122a, 124a, 126a that passes through the slot associated with that band to shorten the band. There may be a fastening region (e.g., region with a fastener complementary with fastening mechanisms 129a, 129b or 129c) disposed on each band 122a, 124a, 126a extending from one end of the band to the other end of the band.

As a non-limiting example, in order to shorten the length of a band (e.g., upper band 126a), the patient can pull the folded portion of the band 126a and couple/attach the pulled folded portion to a point closer to the anterior 110 of the arm 105 or 106 forming a portion of the spine brace system 100 on the fastening region 129a of the band 126a. Similarly, in order to loosen the band (e.g., upper band 126a), the patient can move the folded portion of the band 126a and couple/attach the folded portion to a point closer to the posterior of the arm 105 or 106 forming a portion of the spine brace system 100. Because the bands 122a, 124a and 126a can move independently, the location where a band is folded back on itself and fastened, e.g., fastening mechanism 129a, can be different from the location where the other bands are folded back and fastened, e.g., fastening mechanisms 129b and 129c. Additionally, or in the alternative to the embodiment described above, a hook and loop fastening mechanism may be used for fastening the folded portion of the band 122a, 124a or 126a to the unfolded portion of that band.

Figure 2:
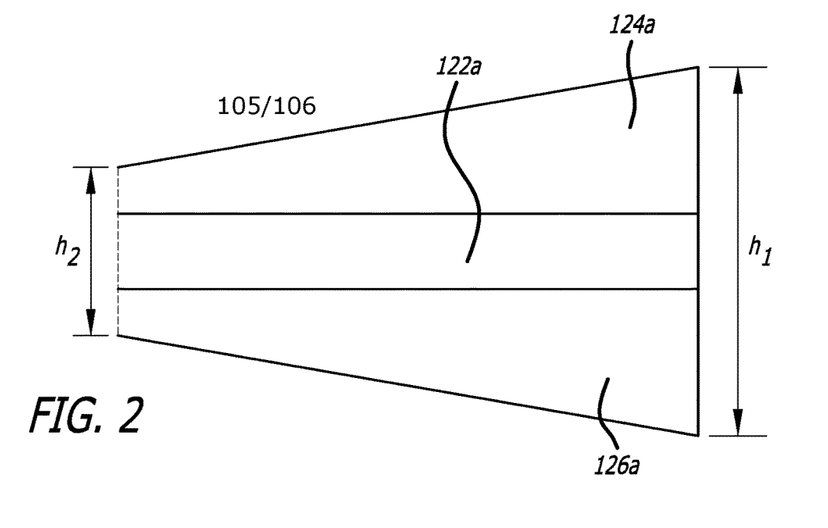
FIG. 2 is an exemplary embodiment of three bands of the adjustable multi-band spine brace system of FIG. 1A and FIG. 1B.

Referring to FIG. 2, a perspective side view of an exemplary embodiment of a spine brace system 100 of FIG. 1A and FIG. 1B is shown. As shown, while the middle band 122a has a substantially constant width, the overall spine brace system 100 is slightly tapered towards its end. As shown, each spine brace arm 105 and 106 is slightly tapered laterally from the one side (e.g., the posterior of the spine brace system 100 as created by tapering of the arm 105/106 of the spine brace system 100) to the other side (e.g., the anterior of the spine brace system 100 as created by tapering of the arm 105/106 of the spine brace system 100).

Figure 3A:
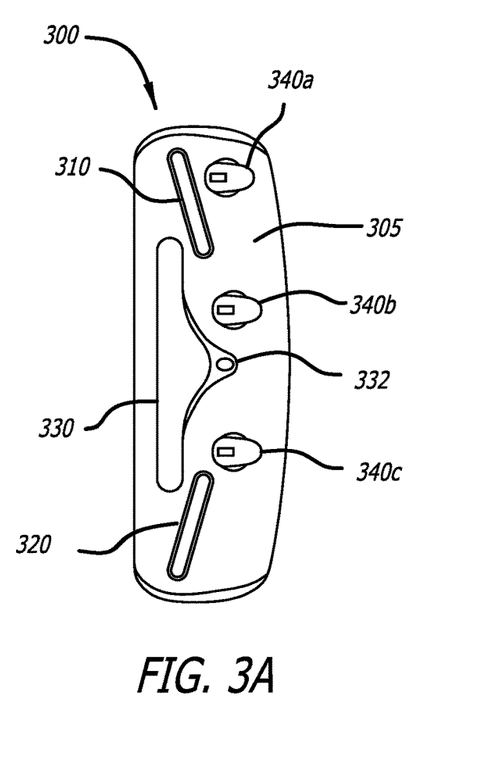
FIG. 3A is a top view of an exemplary embodiment of an adjustment mechanism featuring a pulley system and slots implemented with the adjustable multi-band spine brace system of FIG. 1A and FIG. 1B.
Figure 3B:
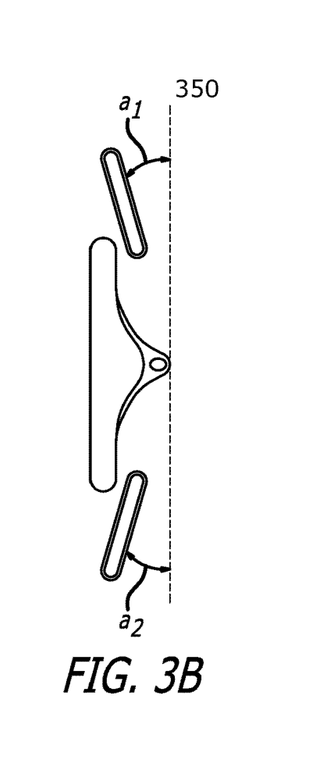
FIG. 3B is a top view of an angled configuration of the upper and lower slots with respect to the middle slot implemented within the adjustment mechanism of the adjustable multi-band spine brace system of FIG. 1A and FIG. 1B.

According to one embodiment of the disclosure, the slightly tapered laterally-extending spine brace system 100 may form as a result of the angled configuration of the upper slot 310 and the lower slot 320 with respect to the middle slot 330 formed as an adjustment mechanism 300 illustrated in FIGS. 3A-3B. In such embodiments, the upper band 124a is extended slightly downward to couple (e.g., "touch") the middle band 122a from the posterior of the brace system 100 towards the anterior of the spine brace system 100 (and anterior portion of arm 105 or 106). This coupling allows the upper band 124a to come into physical contact with the middle band 122a while still retaining their co-planar orientation. Similarly, the lower band 126a is extended slightly upward to couple (e.g., "touch") the middle band 122a from the posterior of the spine brace system 100 to the anterior of the spine brace system 100. As a result, the portion of the spine brace system 100 extending closer to the posterior portion of each arm 105 or 106 has a height $h_1$ which is larger than the height $h_2$ of the portion of the spine brace system 100 extending closer to the anterior portion 110 of the arm 105 or 106.

Herein, as shown in FIG. 2, the band configuration improves the efficiency and comfort of the patient since while the posterior portion and two sides of body of the patient are supported by larger cross section of the spine brace system 100, the abdominal area of the patient, which does not need the support of the spine brace system 100, is covered with a smaller cross section of the spine brace system 100. Moreover, a smaller cross section transforms the unidirectional force exerted by the conventional spine brace to a triangulated force which can increase the stability of each arm 105 and 106, and thus the spine brace system 100 as a whole.

As shown in FIG. 3A, a top view of an exemplary embodiment of an adjustment mechanism 300 featuring a pulley base 305 and slots implemented with the adjustable multi-band spine brace system 100 of FIG. 1A and FIG. 1B is shown. The adjustment mechanism 300 may allow for independent adjustment of the upper band 124a, the middle band 122a, and the lower band 126a is shown. The adjustment mechanism 300 may include a pulley base 305, and a plurality of slots 310, 330, 320, for the upper band 124a, the middle band 122a and lower band 126a of FIG. 1A or FIG. 1B, respectively. In various embodiments, while the pulley base 305 may be used for tightening the spine brace, the plurality of slots 310, 320 and 330 may be used to adjust the bands of the spine brace system 100. The pulley base 305 may include a plurality of pulleys 340a, 340b, 340c disposed and a cord for causing tension to pull complementary pulley base pairs for the arms 105/106 of the spine brace system 100 (not shown).

Referring still to FIG. 3, the (middle) slot 330 for the middle band 122a of FIGS. 1A-1B and FIG. 2 is disposed between the (upper) slot 310 for the upper band 124a of FIGS. 1A-1B and FIG. 2 and the (lower) slot 320 for the lower band 126a of FIGS. 1A-1B and FIG. 2. As shown in FIG. 3B, the upper slot 310 and lower slot 320 may be angled with respect to the middle slot 330, namely angle $a_1$ and angle $a_2$. The angled configuration $a_1$ of the upper slot 310, rotated in a counter-clockwise direction from vertical as shown by a dashed line 350, allows the upper band 122a to extend slightly downward to couple to the middle band 122a from the posterior of the spine brace system 100 to the anterior of the spine brace system 100. Similarly, the angled configuration $a_2$ of the lower slot 320, rotated in a clockwise direction from vertical, allows the lower band 122a to extend slightly upward to couple to the middle band 122a from the posterior of the spine brace system 100 to the anterior of the spine brace system 100. In some embodiments, the clockwise angle of rotation of the lower slot 320 is the same as the counter-clockwise angle of rotation of the upper slot 310. That is, the absolute angular value of a1 is the same as the absolute angular value of a2.

The rotation angle of the upper slot 310 and the rotation angle of the lower slot 320 with respect to the middle slot 330 are so determined that, upon folding each band, a folded portion of the upper band 124a would be fastened to the upper band 124a. Additionally, or in the alternative, a folded portion of the middle band 122a would be fastened to the middle band 122a. Similarly, a folded portion of the lower band 126a would be fastened to the lower band 126a. This ensures that the bands 122a, 124a and 126a, in their folded position, maintain the continuous configuration, in that, the folded upper and folded lower bands come into physical contact with the middle band while still retaining their co-planar orientation.

Figure 4A:
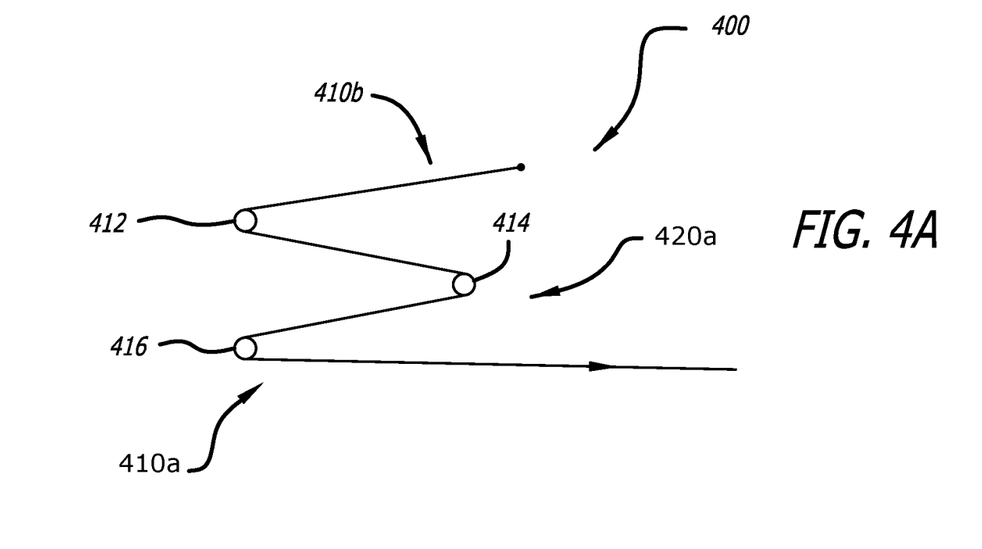
FIG. 4A is a top view of an exemplary embodiment of the first side pulley system implemented with the adjustable multi-band spine brace system of FIG. 1A and FIG. 1B.
Figure 4B:
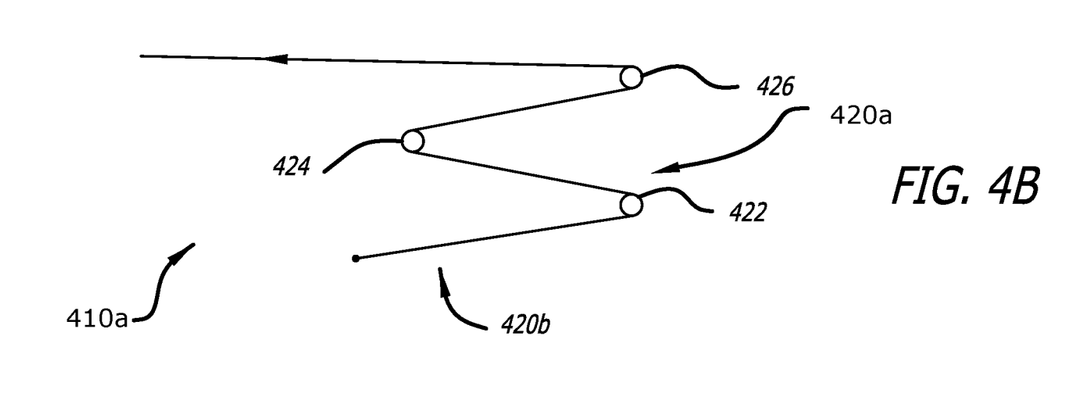
FIG. 4B is a top view of an exemplary embodiment of the second side pulley system implemented with the adjustable multi-band spine brace system of FIG. 1A and FIG. 1B.

FIG. 4A is a top view of an exemplary embodiment of the operability of a first pulley base 410a of a pulley system 400 implemented with the adjustable multi-band spine brace system 100 of FIG. 1A and FIG. 1B. Similarly, FIG. 4B is a top view of an exemplary embodiment of the operability of a second pulley base 420a of the pulley system 400 implemented with the adjustable multi-band spine brace system 110 of FIG. 1A and FIG. 1B. In some embodiments, the adjustment mechanism features a tightening mechanism. The tightening mechanism may include the pulley system 400 to tighten each of the cords on the first arm 105 or second arm 106 of the spine brace system 100, independently.

Herein, the first pulley base 410a of the pulley system 400, represented as pulley base 305 of FIG. 3, may feature a plurality of pulleys (e.g., pulleys 412 and 416) interconnected with a pulley 414 of the second pulley base 420a via a cord (e.g., 410b) as shown in FIG. 4A. The second pulley base 420a, representing a 180° degree x-y axis rotation of the first pulley base 410a features a plurality of pulleys (e.g., 422 and 426) interconnected with a pulley 424 of the first pulley base 410a via the cord (e.g., 420b) as shown in FIG. 4B. The patient can tighten a cord 410b or 420b by pulling the cord 410b or 420b. In some embodiments, the tightening mechanism features one or more of the pulley system 400 in combination with other fastening features such as various the loop and hook fasteners operating in concert. In some embodiments, while the pulleys 412-416 and 422-426 are used to tighten the spine brace system 100, the slots 310, 330 and 320 of FIGS. 3A-3B are used to adjust the length of each band 124a, 122a and 126a of the spine brace system 100 independently.

The pulley system may rely on three pulleys and the cord. That is, the pulleys, an anchor on the pulley base, and the cord form a 4:1 pulley system. In such 4:1 pulley system configurations, a first end of the cord is coupled directly to the middle band and enters a first end of the adjustment mechanism 300. After passing through designated pulleys, the cord 410b or 420b extends outwardly from a second end of the adjustment mechanism. In such embodiments, tightening of the spine brace system 100 is performed by pulling the second end of the cord 410b or 420b.

In some embodiments, two tightening mechanisms, each featuring a pulley system, are disclosed. A first tightening mechanism allows for independent tightening of the middle band of the first arm of the spine brace system. With a two-tightening mechanism configuration, once the patient tightens the middle band of a particular arm of the spine brace, the corresponding portion of the tightening mechanism of the two tightening mechanism becomes closer to the other tightening mechanism. Alternatively, when the patient tightens both tightening mechanisms, the entire two tightening mechanisms become closer together.

Referring back to FIG. 3A, in some embodiments, a lower part of the upper slot 310 may be arranged to slightly overlap with an upper part of the middle slot 330 so that the upper slot 310 is interposed between the middle slot 330 and a first pulley 340a mounted on the pulley base 305. In some embodiments, an upper part of the lower slot 320 may be arranged to slightly overlap with a lower part of the middle slot 330 so that the upper part of the lower slot 320 is interposed between the middle slot 330 and a third pulley 340c mounted on the pulley base 305. The middle slot 330 may have an opening 332, referred to as a T-shaped opening. The T-shaped opening 332 facilitates adjustment of the middle band 122a of FIGS. 1A-1B and FIG. 2. The T-shaped opening 332 narrows slightly in a center region of the tightening mechanism which can further guide a cord.

In some embodiments, the spine brace system 100 may include a middle cord 122b for adjusting tension of the middle band 122a. In such embodiments, the spine brace system further includes the adjustment mechanism that has slots for the middle band 122a. In some embodiments, the tightening mechanism includes slots for each of the upper, middle and lower bands. Optionally, the upper and lower slots may be angled with respect to the middle slot.

Referring back to FIG. 4A and FIG. 4B, as shown, the first pulley base 410a is associated with a tightening mechanism which is configured to tighten the first arm 105 of the spine brace system 100 (see FIG. 1A). Similarly, the second pulley base 420a is associated with the tightening mechanism, which is configured to tighten the second arm 106 of the spine brace system 100 (see FIG. 1B). Each pulley base 410a or 420b relies on a cord and a plurality of pulleys. For example, the first pulley base 410a includes the first cord 410b and the first plurality of pulleys 412, 414 and 416. By tightening the first cord 410b that passes through each of the pulleys 412, 414 and 416, the patient can tighten the first arm 105 of the spine brace system 100. Similarly, the second pulley base 420a includes the second cord 420b and the second plurality of pulleys 422, 424 and 426. By tightening the second cord 420b that passes through each of the pulleys 422, 424 and 426, the patient can tighten the second arm 106 of the spine brace system 100.

Figure 5:
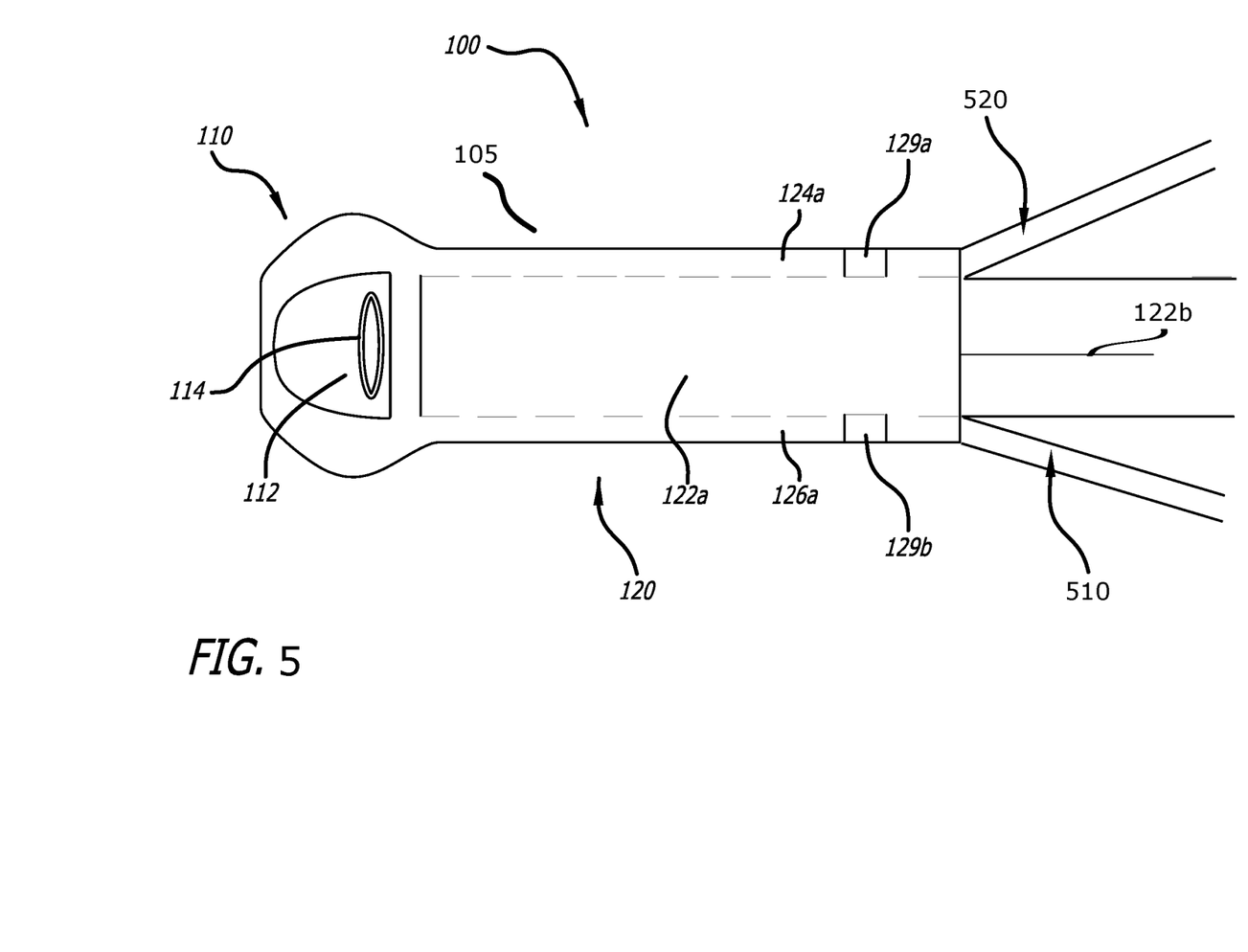
FIG. 5 is a perspective outside view of an exemplary embodiment of an adjustable multi-band spine brace system.

FIG. 5 is a perspective outside view of an exemplary embodiment of an adjustable multi-band spine brace system. In some embodiments, when worn, the band 122a and 124a are so arranged that one edge of the upper band 124a is in contact with one edge of the middle band 122a while the upper band 124a and the middle band 122a do not overlap. Similarly, the band 122a and 126a may be so arranged that one edge of the lower band 126a is in contact with one edge of the middle band 122a while the lower band 126a and the middle band 122a do not overlap. Additionally, or in the alternative, in some embodiments, when worn, the band 122a and 124a are so arranged that the upper band 124a and the middle band 122a overlap in the lateral portion 120. Similarly, the band 122a and 126a may be so arranged that the lower band 126a and the middle band 122a overlap in the lateral portion 120.

In some embodiments, the upper band 124a and the middle band 122a are so arranged that portions of the upper band 124a extending towards the posterior portion of the spine brace 100 are separate from portions of the middle band 122a extending towards the posterior portion of the spine brace 100, as shown by the region 520 in FIG. 5. Additionally, or in the alternative, in some embodiments, the lower band 126a and the middle band 122a are so arranged that portions of the lower band 126a extending towards the posterior portion of the spine brace 100 are separate from portions of the middle band 122a extending towards the posterior portion of the spine brace 100, as shown by the region 510 in FIG. 5.

In the foregoing description, the invention is described with reference to specific exemplary embodiments thereof. For example, the telescopic lateral panels and adjustable belt member combination, operating with a pulley subsystem, may be deployed within a LSO orthopedic brace with an architecture different than the orthopedic brace described above. Hence, it will be evident that certain components may be deployed within different types of orthopedic braces and various modifications and changes may be made thereto without departing from the broader spirit and scope of the invention as set forth in the appended claims.

What is claimed is:

1. A spine brace comprising:
   a first band formed of a first middle band disposed between a first upper band and a first lower band, the first middle band includes a posterior portion configured to reside against a back of a wearer; and
   a pulley system physically separate and independent from the first band, the pulley system including a first cord, a first pulley base moveable in response to movement of the first cord to cause tightening of the first band and a second pulley base, wherein the first pulley base, physically separate and independent from the second pulley base, includes at least a first upper slot adapted to receive the first upper band, a first lower slot adapted to receive the first lower band, and a plurality of pulleys, wherein the first upper slot and the first lower slot are disposed with a first angle toward a center of the pulley system,
   wherein the first cord is fixedly connected to the first pulley base and the second pulley base and looped around a first subset of the plurality of pulleys, and
   wherein a rotation angle of the first upper slot is set to allow a folded portion of the first upper band inserted through the first upper slot to be fastened back to the first upper band and a rotation angle of the first lower slot is set to allow a folded portion of the first lower band inserted through the first lower slot to be fastened back to the first lower band.

2. The spine brace of claim 1, further comprising:
   the first upper band and the first lower band are disposed above and below the first middle band, respectively.

3. The spine brace of claim 1, wherein the first upper slot and the first lower slot are so angled with respect to a first middle slot so that,
   the folded portion of the first upper band is fastened to the first upper band,
   a folded portion of the first middle band is fastened to the first middle band, and
   the folded portion of the first lower band is fastened to the first lower band.

4. The spine brace of claim 1, wherein the first pulley base includes a plurality of slots including a first middle slot uniquely associated with the first middle band, the first upper slot uniquely associated with the first upper band, and the first lower slot uniquely associated with the first lower band.

5. The spine brace of claim 4, wherein the first upper slot for the first upper band and the first lower slot for the first lower band are angled with respect to the first middle slot for the first middle band.

6. The spine brace of claim 4, wherein the first middle slot for the first middle band includes an opening that narrows at a center region of the opening and is longer in length than an opening of the first upper slot associated with the first upper band and the first lower slot associated with the first lower band.

7. The spine brace of claim 4, wherein the first upper band is configured to be independently tightened from the first lower band and the first middle band by changing a size of the folded portion of the first upper band inserted through and securely attached to the first upper slot.

8. The spine brace of claim 1, wherein the first upper slot is rotated in a counter-clockwise direction from vertical to allow the first upper band to extend downward to couple to the first middle band.

9. The spine brace of claim 8, wherein the first lower slot is rotated in a clockwise direction from vertical to allow the first lower band to extend upward to couple to the first middle band.

10. The spine brace of claim 1, wherein the first pulley base comprises a first middle slot positioned between the first upper slot and the first lower slot in which a first pulley and a second pulley of the plurality of pulleys are positioned laterally behind the first middle slot, the first middle slot for receiving the first middle band.

11. The spine brace of claim 10, wherein the first middle slot features a T-shaped opening with the first pulley positioned behind a first half of the T-shaped opening and the second pulley positioned behind a second half of the T-shaped opening.

12. A spine brace comprising:
a first band formed of a first middle band between a first upper band and a first lower band, the first middle band includes a posterior portion configured to reside against a back of a wearer; and
a first pulley system physically separate and independent from the posterior portion of the first band, the first pulley system including a first pulley base in which movement of a first cord causes tightening of the first band and a second pulley base that is a separate component from the first pulley base and movable independent of movement of the first pulley base,
wherein the first pulley base comprises a plurality of pulleys, a first upper slot adapted to receive the first upper band, a first lower slot adapted to receive the first lower band, and a first middle slot adapted to receive the first middle band,
wherein the first upper slot is angled downward at a first angle with respect to the first middle slot and the first lower slot is angled upward at a second angle with respect to the first middle slot, and
wherein the first angle is set to allow a folded portion of the first upper band inserted through the first upper slot to be fastened back to the first upper band and the second angle of the first lower slot is set to allow a folded portion of the first lower band inserted through the first lower slot to be fastened back to the first lower band.

13. The spine brace of claim 12, wherein the first upper band and the first lower band are disposed above and below the first middle band, respectively.

14. The spine brace of claim 12, wherein the first upper slot and the first lower slot are angled with respect to the first middle slot so that,
the folded portion of the first upper band is fastened to the first upper band,
a folded portion of the first middle band is fastened to the first middle band, and
the folded portion of the first lower band is fastened to the first lower band.

15. The spine brace of claim 12, wherein the first middle slot for the first middle band includes an opening that narrows at a center region of the opening and is longer in length than an opening of the first upper slot associated with the first upper band and an opening of the first lower slot associated with the first lower band.

16. The spine brace of claim 12, wherein the first upper band is configured to be independently tightened from the first lower band and the first middle band by changing a size of the folded portion of the first upper band inserted through and securely attached to the first upper slot.

17. The spine brace of claim 12, wherein the first upper slot is rotated in a counter-clockwise direction from vertical to allow the first upper band to extend downward to couple to the first middle band.

18. The spine brace of claim 17, wherein the first lower slot is rotated in a clockwise direction from vertical to allow the first lower band to extend upward to couple to the first middle band.

19. The spine brace of claim 12, wherein the first middle slot of the first pulley base is positioned between the first upper slot and the first lower slot in which a first pulley and a second pulley of the plurality of pulleys are positioned laterally behind the first middle slot.

20. The spine brace of claim 19, wherein the first middle slot features a T-shaped opening with the first pulley positioned behind a first half of the T-shaped opening and the second pulley positioned behind a second half of the T-shaped opening.

21. The spine brace of claim 1, further comprising:
a second band formed of a second middle band disposed between a second upper band and a second lower band; and
a second cord fixedly connected to the first pulley base and the second pulley base and looped around a second subset of the plurality of pulleys, wherein tightening movement of the second cord causes movement of the second pulley base.

22. The spine brace of claim 1, wherein the first upper slot is disposed between a first middle slot and a first pulley of the plurality of pulleys.

* * * * *